United States Patent [19]

Mawson

[11] Patent Number: 5,453,565
[45] Date of Patent: Sep. 26, 1995

[54] ASTAXANTHIN FROM FLOWERS OF THE GENUS ADONIS

[75] Inventor: Rodney Mawson, Thrapston, Great Britain

[73] Assignee: Unilever Patent Holdings B.V., Vlaardingen, Denmark

[21] Appl. No.: 321,100

[22] Filed: Oct. 11, 1994

Related U.S. Application Data

[63] Continuation of Ser. No. 956,500, filed as PCT/GB91/01182, July 17, 1991.

[30] Foreign Application Priority Data

Jul. 20, 1990 [GB] United Kingdom .................... 9016012

[51] Int. Cl.⁶ ............................... A01H 5/00; A01H 5/10; C07C 403/00
[52] U.S. Cl. .................... 800/200; 800/255; 800/DIG. 9; 585/351
[58] Field of Search ................................... 800/200, 250, 800/255, DIG. 9; 585/351; 536/124, 127, 128; 426/540; 119/3

[56] References Cited

U.S. PATENT DOCUMENTS 4,141,994  2/1979  Aneja et al. ............................. 424/331

FOREIGN PATENT DOCUMENTS 9005765  5/1990  WIPO .

OTHER PUBLICATIONS

Kamata, T., Thesis entitled "Study of Astaxanthin Diester in the Flower Adonis . . . of Rainbow Trout Salmo Gairdneri", 1985.
Renstrom et al, Biochem. Systematics and Exology, 9(4):2490250 (1981).
Seybold et al. 1959. Nature. 184:1714–1715.
Bailey, 1935. The Standard Cyclopedia of Horticulture. pp. 220–221.
Bailey et al. 1976. Hortus Third. p. 27.
Kamata et al. 1987. Comp. Biochem. Physiol. 86B(3):587–591.

*Primary Examiner*—David T. Fox
*Assistant Examiner*—Erich E. Veitenheimer
*Attorney, Agent, or Firm*—Cushman Darby & Cushman

[57] ABSTRACT

A novel strain of *Adonis aestivalis* having an average of 18–22 petals per flower head and containing an average of 200–350 µg of astaxanthin pigment per flower head is cultivated, harvested and extracted to provide a source of natural astaxanthin. The extracted astaxanthin, or the harvested astaxanthin-containing plant material, can be used for example in salmonid fish diets to promote correct flesh pigmentation of the fish.

7 Claims, No Drawings

ASTAXANTHIN FROM FLOWERS OF THE GENUS ADONIS

This is a continuation of application Ser. No. 07/956,500, filed as PCT/GB91/01182, July 17, 1991, which was abandoned upon the filing hereof.

BACKGROUND OF THE INVENTION

This invention relates to carotenoid pigments extractable from natural sources.

There is a need for a cost-effective natural source of astaxanthin, which is the carotenoid pigment that contributes the characteristic pink or red colour to the flesh of wild salmon. Salmonid fish are extensively farmed today, and there is a commercial need to produce such fish possessing a nature-identical flesh colour.

Astaxanthin occurs in various marine animals, such as crustacea, but its extraction from such sources is uneconomic. It is also possible to synthesise astaxanthin, but this is expensive, and moreover the use of such synthetic pigment does not convey the connotation of 'natural' that many consumers regard as desirable.

Astaxanthin occurs in certain plants, especially certain species belonging to the genus Adonis. One such species is *Adonis aestivalis*, where it occurs predominantly in the petals of the bright red flowers. However, the reported wild strains of *Adonis aestivalis* possess only flower heads with very few petals, and the proportion of astaxanthin pigment relative to the total mass of the plant is too small for it to be cultivated and extracted on any sensible commercial scale.

SUMMARY OF THE INVENTION

By the invention we have discovered a novel true-breeding strain of *Adonis aestivalis* having substantially heavier flower heads, and in particular having a substantially greater number of petals. The proportion of astaxanthin pigment in the plant is sufficiently high to make cultivation of the plant for the purposes of extracting the pigment commercially attractive.

The invention provides plants of the genus Adonis having petals containing astaxanthin, the average number of petals per flower head being at least 10, more particularly at least 16.

The invention also provides plants of the genus Adonis having petals containing astaxanthin, wherein the amount of astaxanthin per flower head is at least 100 µg, more particularly at least 150 µg, and yet more particularly at least 200 µg.

The invention includes the cultivation of such plants for the purpose of obtaining astaxanthin, the extraction of astaxanthin from such plants, and the astaxanthin so obtained.

Extraction of the astaxanthin is preferably conducted using an organic solvent, and more preferably using a mixed solvent comprising a water-miscible organic solvent (such as ethanol) and a non-water-missible organic solvent (such as hexane).

Preferably, the harvested plant material is initially extracted with water or aqueous media to remove water soluble compounds such as glycosides.

The invention particularly provides a process for obtaining astaxanthin, wherein plants of the species *Adonis aestivalis* having an average flower head petal number of at least 16 are cultivated, harvested, and the astaxanthin is extracted from the harvested flower heads or petals thereof.

An important embodiment of the invention is a newly-discovered strain of *Adonis aestivalis* of which a seed sample has been deposited on 18 July 1990 with the National Collection of Industrial and Marine Bacteria Limited, Aberdeen, under Accession No. NCIMB 40309, in accordance with the provisions of the Budapest Treaty. The invention encompasses plants of the species *Adonis aestivalis* having the essential characteristics of this deposited strain. Plants of this deposited strain typically have an average of 18–22 petals per flower head, and the average amount of astaxanthin per flower head is 200–350 µg.

The invention also provides a process for obtaining astaxanthin, wherein the astaxanthin is extracted from the petals of plants having the essential characteristics of the deposited strain.

The invention particularly provides an oral composition for administration to fish, comprising such extracted astaxanthin, and a method of pigmenting the flesh of fish, especially salmonid fish, involving the oral administration to the fish of such a composition.

Preferably, the composition comprises the astaxanthin mixed with edible feed material. Alternatively, the astaxanthin can be in encapsulated form.

Alternatively, pigmentation of the flesh of fish can be achieved by feeding astaxanthin-containing portions of the plant to the fish. Preferably, the portion comprises the flower petals and more preferably, consists entirely of such material. If desired, the plant material can be extracted with water or aqueous media in order to remove water-soluble compounds such as glycosides which may be toxic to fish or other animals, without removing significant quantities of the required astaxanthin.

In the pigmentation of farmed fish, the astaxanthin obtained by the invention can be administered orally to the fish in any manner analogous to the techniques already used for astaxanthin derived from conventional sources. Normally the pigment is included in a composition, such as a pelleted compound feedstuff, that forms all or part of the diet on which the fish are reared. The pigment is soluble in oil, and can be incorporated in the diet in this form, either as free oil or as encapsulated oil. Alternatively, the petals or other plant material containing the astaxanthin can be mixed (e.g. in dried, ground form) with conventional fish feed ingredients. If desired, the plant material can be partially extracted with aqueous media (to remove water-soluble components such as glycosides) prior to being added to the feed. As a further alternative, the pigment can be added to the feed in the form of an organic solution, e.g. a solution obtained during extraction of the astaxanthin from the plant material, if the organic solvent used is not toxic to the fish in any amount that the fish are likely to ingest via the completed feedstuff.

When the astaxanthin is administered to fish via their feedstuff, the composition of the feedstuff need not be unconventional. The feedstuff formulation can contain any of the normal fish feed components, such as fish meal and/or other protein, oil such as fish oil, cereals, vitamins, minerals, preservatives and medicaments, in the various proportions that are normally used.

The extracted astaxanthin, or astaxanthin-containing portions of the plant, can also be used as a colouring agent in human foodstuffs, and also in poultry diets to enhance the colour of egg yolks.

DESCRIPTION OF THE PREFERRED EMBODIMENTS

Specific embodiments of the invention will now be described in detail, by way of example only.

Novel strain of *Adonis aestivalis*

The essential characteristics of the newly-discovered strain are:

Chromosome No. $2n=32$

Erect, annual, leaves alternative, pinnately dissected into linear or filiform segments. Flowers bright red, actinomorphic, hypogynous, hermaphrodite, solitary and terminal on stem and branches.

Petals less than 15mm long, up to 2 times length of sepals. Sepals 5–8 in number. Petals 18–22 in number.

Values for these parameters, and for the astaxanthin level per flower head, can be taken from analysis of the first fully-open flower heads from 1000 plants.

Ripe achenes 3–5 mm, tooth on dorsal surface distant from the beak. Achenes having a transverse ridge passing around middle of achene. Achenes also having a dorsal hump a distance from the beak.

Cultivation

The plant can be grown under a wide range of temperature conditions. Germination requires a degree of alternating temperatures of 10–20° C. Mature flowering plants are obtained four months after sowing at field densities up to 150 plants/m$^2$ in a variety of soil conditions; flowering in the summer months (temperate climate). The plant prefers dry, well drained conditions. Seed can be harvested by combine, and flowers by hand.

Extraction of pigment

Pigment can be extracted by solvent extraction, e.g. into mixed solvents such as ethanol/hexane, and further purified by partitioning a mixed solvent with water followed by column chromatography. The final extract, thus purified, is rich with respect to carotenoids, and predominent is astaxanthin, present mainly as a racemic mixture in the form of mono- and diesters, generally of palmitic acid.

Typical starting material

Frozen block of flower heads, stored at −20° C. in the dark, or dried petals/flowerheads, finely ground, also stored at low temperature in the dark.

Primary Extraction

Mix with 10 vols hexane/ethanol (50:50 v/v), allow dispersion, and homogenise for 10 minutes in dark and cool conditions using shear blender; or mill with a shear blender in ethanol, then add hexane for safety reasons.

Leave overnight in dark and cool conditions.

Filter through filter (e.g. muslin) on vibrating sieve, and wash plug with 50:50 ethanol:hexane. Retain original filtered liquid and washings as primary extract. This primary extract contains water-soluble, ethanol-soluble and hexane-soluble material including pigments and glycoside.

Secondary Extraction

Add 1 part water to 2.5 parts primary extract, transfer to phase separator and remove bottom layer of ethanol. Wash upper hexane layer with 1:1 ethanol/water mixture allow to separate and discard lower layer.

Transfer to steam jacketed vacuum evaporator (with cyclone) and remove hexane at 45° C. for 15–30 minutes until a sludge is obtained. Wash with ethanol and evaporate, wash with hexane and evaporate (again at low temperatures, under vacuum or under nitrogen) to dryness. This yields a first concentrate of approximately 5% total pigment (80% astaxanthin) in dry matter. Take up in hexane and apply to silica column (1:1 or 2:1 extract to silica). Wash column with hexane in dark and cool conditions, and discard washings. Elute with 2.5% ethanol in hexane until a red-orange band appears. Collect the red-orange washings until the colour changes to orange-green. Dry eluent as before, take up in hexane or oil (fish oil, vegetable oil). This yields a second concentrate of approximately 20% total pigment containing approximately 80% astaxanthin.

| Typical Salmon Grower Diet | |
|---|---|
| | % inclusion by weight |
| Fishmeal | 75.0 |
| Vegetable protein | 5.0 |
| Cereal | 7.8 |
| Fish oil | 11.0 |
| Minerals/Vitamins | 1.0 |
| Antioxidants/preservatives | 0.2 |

Pigment incorporation

Astaxanthin pigment from an Adonis strain of the invention can be added at levels ranging for example from 1–100 ppm to the above type of diet in a variety of ways:

a) as extracted astaxanthin carried in a fish oil base, optionally containing antioxidants.

b) as extracted astaxanthin carried as a free-flowing powder in wheatflour or any finely ground foodstuff for salmon.

c) as for (b) but encapsulated in alginate, gelatin or xanthan gum, eg. by pan granulation or spray cooling.

d) as extracted astaxanthin carried in an encapsulated lipid, eg. casein-protected lipid.

Pigmentation

The above typical salmon grower formulation containing 50–100 ppm of astaxanthin extracted from the deposited Adonis strain of the invention and carried in one of the product forms described above, is fed as pellets to fish of 300 g liveweight plus for a minimum period of 3 months. Typical values for pigmentation efficiency, compared with commercially-available synthetic astaxanthin, are at least about 80% of synthetic.

The skilled reader will readily appreciate that the foregoing extraction procedures, diet formulations, feeding regimes and other details may be subject to considerable variation without departing from the scope of the invention as claimed herein.

What is claimed:

1. A process for the production of astaxanthin pigment which comprises cultivating plants of the genus Adonis having an average of at least 16 red petals per flower head, harvesting said plants and extracting the astaxanthin therefrom.

2. A process according to claim 1, wherein the astaxanthin is extracted from plants of the species *Adonis aestivalis* having an average of 18 to 22 petals per flower head.

3. A process for the production of astaxanthin wherein the astaxanthin is extracted from plants of the strain NCIMB 40309.

4. A process according to claim 1 or claim 3, involving cultivation of the plants, harvesting of the flower heads and extraction of the astaxanthin from the harvested flower heads or petals thereof.

5. A process according to claim 1 or claim 3, wherein the extraction of the astaxanthin is conducted using an organic solvent.

6. A process according to claim 5 wherein the extraction is conducted using a mixed solvent comprising a water-miscible organic solvent and a non-water-missible organic solvent.

7. A process according to claim 5, wherein the harvested plant material is initially extracted with water or aqueous media to remove water soluble compounds such as glycosides.

* * * * *